United States Patent
Hayman et al.

(10) Patent No.: US 6,511,472 B1
(45) Date of Patent: Jan. 28, 2003

(54) INTERFACE NEEDLE AND METHOD FOR CREATING A BLUNT INTERFACE BETWEEN DELIVERED LIQUIDS

(75) Inventors: Douglas R. Hayman, Mission Viejo, CA (US); Ed Olsen, Lake Forest, CA (US); Noah M. Roth, Irvine, CA (US); Gary Curri, Fallbrook, CA (US); Thomas J. Whalen, II, Encinitas, CA (US)

(73) Assignee: MicroTherapeutics, Inc., Irvine, CA (US)

( * ) Notice: Subject to any disclaimer, the term of this patent is extended or adjusted under 35 U.S.C. 154(b) by 0 days.

(21) Appl. No.: 09/574,392

(22) Filed: May 19, 2000

Related U.S. Application Data

(60) Provisional application No. 60/135,286, filed on May 21, 1999.

(51) Int. Cl.[7] .............................................. A61M 39/00
(52) U.S. Cl. ........................................................ 604/533
(58) Field of Search ................................ 604/523, 533, 604/534, 535, 538

(56) References Cited

U.S. PATENT DOCUMENTS

| | | | |
|---|---|---|---|
| 1,015,276 A | 1/1912 | Rowse | |
| 1,944,553 A | 1/1934 | Freund | |
| 4,187,848 A | 2/1980 | Taylor | 128/247 |
| 4,354,490 A | 10/1982 | Rogers | 128/213 |
| 4,423,741 A | 1/1984 | Levy | 128/768 |
| 4,543,094 A | 9/1985 | Barnwell | 604/236 |
| 4,687,475 A | 8/1987 | Tai et al. | 604/248 |
| 4,693,710 A | 9/1987 | McCool | 604/283 |
| 4,963,132 A | 10/1990 | Gibson | 604/256 |
| 5,263,945 A | 11/1993 | Byrnes et al. | 604/283 |
| 5,413,115 A | 5/1995 | Baldwin | 128/763 |
| 5,423,776 A | 6/1995 | Haindl | 604/283 |
| 5,439,452 A | 8/1995 | McCarty | 604/248 |
| 5,509,911 A | 4/1996 | Cottone, Sr. et al. | 604/283 |
| 5,549,583 A | 8/1996 | Sanford et al. | 604/283 |
| 5,609,584 A | 3/1997 | Gettig et al. | 604/283 |
| 5,624,414 A | 4/1997 | Boettger | 604/283 |
| 5,782,505 A | 7/1998 | Brooks et al. | 285/175 |
| 5,827,244 A | 10/1998 | Boettger | 604/283 |
| 5,899,888 A | 5/1999 | Jepson et al. | 604/201 |
| 5,989,240 A | 11/1999 | Strowe | 604/533 |

*Primary Examiner*—Sharon Kennedy
(74) *Attorney, Agent, or Firm*—Burns, Doane, Swecker & Mathis L.L.P.

(57) ABSTRACT

An interface needle is used for connecting a syringe to a catheter to create a blunt interface between two or more liquids being delivered through the catheter. The interface needle is particularly useful for creating a blunt interface between a biocompatible solvent and a liquid embolic composition which is delivered to the body for treatment of various conditions including aneurysms. A system for liquid delivery with a blunt liquid interface includes a catheter or other cannula, an interface needle, and a syringe. The interface needle includes a tube extending from a distal end which delivers liquid to a lumen of the catheter bypassing a reservoir in the catheter hub to create the blunt liquid interface. One embodiment of the interface needle controls an injection pressure of high viscosity liquids.

19 Claims, 2 Drawing Sheets

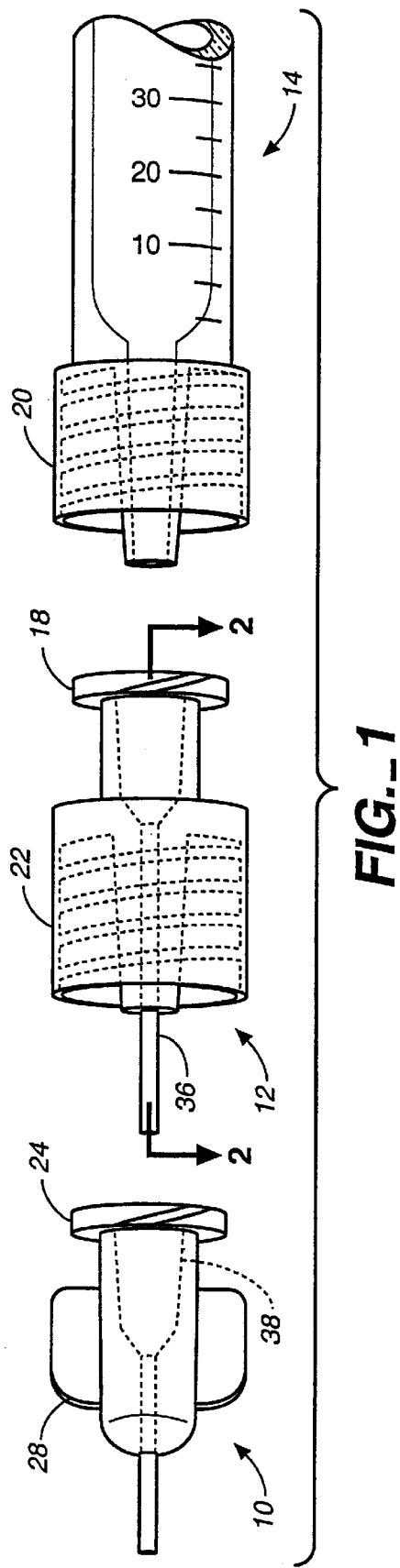
FIG._1

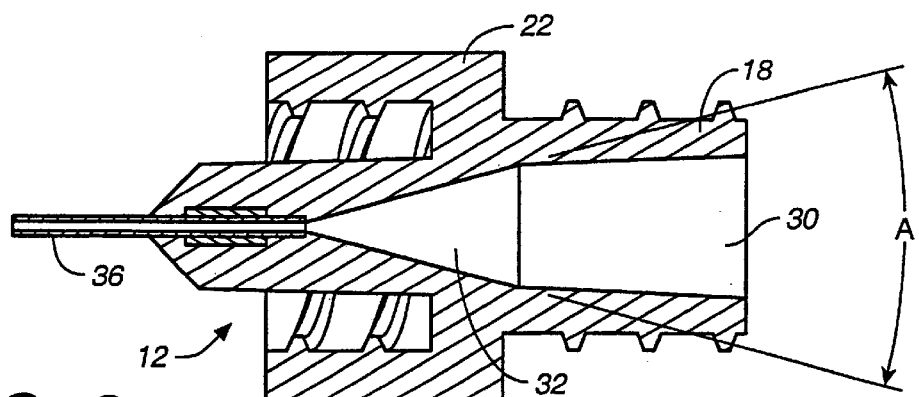
FIG._2
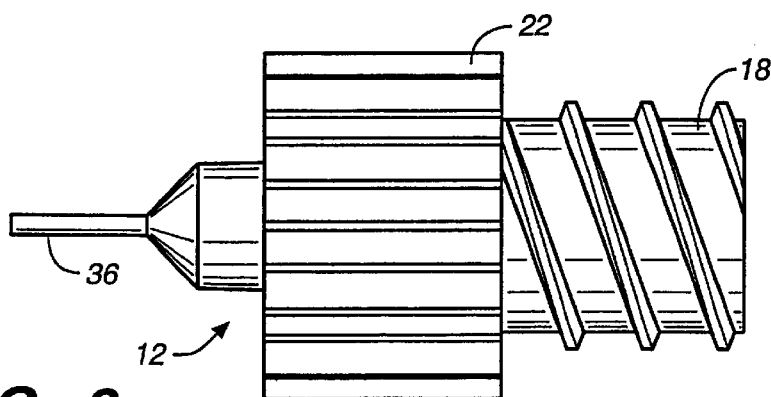
FIG._3
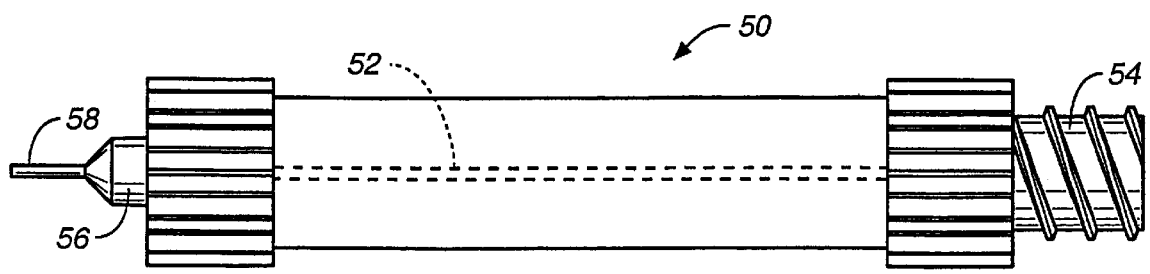
FIG._4

INTERFACE NEEDLE AND METHOD FOR CREATING A BLUNT INTERFACE BETWEEN DELIVERED LIQUIDS

This application claims priority based on U.S. Provisional Application Ser. No. 60/135,286 filed on May 21, 1999 which is incorporated herein by reference in its entirety.

BACKGROUND OF THE INVENTION

1. Field of the Invention

The invention relates to an interface needle, and more particularly, the invention relates to an interface needle for connecting a syringe to a catheter to create a blunt interface between liquids being delivered through the catheter.

2. Brief Description of the Related Art

The delivery of fluid compositions which solidify in vivo is particularly useful for a variety of reasons including treatment of blood vessels, tumors, aneurysms, arteriovenous malformations ("AVMs"), arteriovenous fistula ("AVF"), uncontrolled bleeding and the like, as well as in the sterilization of mammals by blocking the vas deferens or fallopian tubes, in the treatment of urinary incontinence by the addition of a bulking agent to the periurethral tissue, and the like.

Delivery of such compositions is preferably accomplished via catheter techniques which permit the selective placement of the catheter at the delivery site. For example, recent advancements in catheter technology as well as in angiography now permit neuro endovascular intervention including the treatment of otherwise inoperable lesions. Specifically, development of microcatheters and guidewires capable of providing access to vessels as small as 1 millimeter in diameter allows for the endovascular treatment of many lesions.

Fluid compositions which are delivered for in vivo solid mass formation generally include a solvent such as ethanol, acetone, ethyl lactate, dimethylsulfoxide ("DMSO"), or aqueous solutions of ethanol or DMSO, a biocompatible water insoluble polymer, and a water insoluble contrast agent. Preferably, however, the solvent is non-aqueous in order to maximize the amount of biocompatible water insoluble polymer which can be dissolved therein. Once delivered, the solvent dissipates from the polymer forming a solid polymer mass.

In practice, the catheter tip is directed to the vascular or other delivery site by use of conventional visualization techniques such as fluoroscopy, and the like which allow the clinician to visualize and direct the catheter tip. After placement of the catheter, the composition is introduced into the catheter with a syringe and delivered to the delivery site by the catheter. Upon delivery, the solvent dissipates into the blood, fluid, or tissue and the water insoluble polymer precipitates to form a coherent mass which solidifies in vivo.

One use of this liquid embolic polymer composition is in minimally invasive procedures for treating intracranial aneurysms. The use of liquid embolic compositions addresses the problems with the known aneurysm treatment methods, such as surgical clipping and coil delivery, and involves the endovascular injection of the liquid embolic composition which solidifies in the aneurysm to occlude the aneurysm. Typically, the liquid embolic composition will include a water insoluble, biocompatible, non-biodegradable polymer dissolved in a biocompatible solvent. Once the liquid embolic composition is injected into the aneurysm, the biocompatible solvent dissipates into the blood and the polymer solidifies to occlude the blood flow into the aneurysm. These liquid embolic compositions preferably include a radiopaque material or contrast agent which allows the physician to view the embolization procedure by fluoroscopy or other visualization techniques.

The liquid embolic composition is delivered to the catheter with a syringe connected to the catheter hub. Often the liquid embolic composition is delivered after an aqueous solution such as an aqueous solution containing a contrast agent which is used to visualize blood flow at the aneurysm site. After delivery of an aqueous contrast solution or other aqueous solution the catheter is then flushed with the biocompatible solvent. Flushing with the biocompatible solvent will prevent the catheter line from become plugged due to premature precipitation of the biocompatible polymer in the presence of the aqueous solution. However, when delivery of the biocompatible solvent is followed by delivery of the liquid embolic composition this results in some mixing of the liquid embolic composition and the biocompatible solvent at a liquid interface. The mixing results in a diluted polymer composition having a low viscosity which is difficult to deliver and tends to form strands upon delivery. Strands of the polymer composition may be carried away in the blood stream where the polymer can occlude an undesired vascular location. In addition, the mixed liquid at the liquid interface makes it difficult to detect the first appearance of the polymer composition in vivo.

Accordingly, it would be desirable to provide a delivery system for reducing mixing of two sequentially delivered liquids, such as a biocompatible solvent and a liquid embolic composition.

In addition, it is difficult to deliver liquid embolic compositions of a biocompatible polymer, a biocompatible solvent, and a biocompatible contrast agent including greater than eight weight percent polymer, based on the entire weight of compositions through conventional neuro catheter delivery systems because these high viscosity compositions require high pressures for injection that may rupture the catheter system. However, in some instances it is desirable to deliver higher viscosity embolic compositions, for example compositions containing more than eight weight percent of a polymer. These higher viscosity embolic compositions are generally easier to position within an aneurysm. The higher viscosity may also help to prevent portions of the polymer from being separated from the polymer mass and being carried away in the blood stream where the polymer can occlude an undesired vascular location.

Accordingly, it would be desirable to provide a delivery system for delivery of high viscosity liquids through small lumens while preventing rupture of the delivery system.

SUMMARY OF THE INVENTION

The present invention relates to a device, system, and method for establishing a blunt interface between two delivered liquids.

The invention also relates to a device, system, and method for delivering high viscosity fluid through a vascular delivery system.

According to one aspect of the present invention, a device for creating a blunt interface between delivered liquids includes a body having a proximal end configured for connection to a syringe and a distal end opposite the proximal end configured to be attached to a cannula hub. A tapered lumen extends through the body from the proximal end to the distal end and the lumen has a first diameter at the proximal end and a second smaller diameter at the distal end. A tube extends from the distal end of the body and delivers liquid directly to a lumen of the cannula bypassing a reservoir in the cannula hub.

According to another aspect of the present invention, a system for creating a blunt interface between delivered liquids includes a syringe; a cannula having a cannula lumen, a cannula hub with a female luer fitting, and a reservoir within the cannula hub; and a bypass device connectable to the syringe and the cannula hub. The bypass device has a tube for delivering liquid directly to the lumen of the cannula bypassing the reservoir in the cannula hub.

In accordance with a further aspect of the present invention, a method of delivering two liquids includes the steps of delivering a first liquid through a cannula with a first syringe, removing the first syringe from the cannula, attaching a second syringe to a bypass device for creating a blunt liquid interface, connecting the bypass device to the cannula, and delivering a second liquid with the second syringe to create a blunt liquid interface between the first and second liquids.

The present invention provides advantages of reducing mixing and providing a blunt interface between two delivered liquids.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 1 is an exploded side view of a catheter, interface needle, and syringe system;

FIG. 2 is a cross sectional view of the interface needle, taken along line 2—2 of FIG. 1;

FIG. 3 is a side view of the interface needle; and

FIG. 4 is a side view of an interface needle according to an alternative embodiment of the invention for delivery of high viscosity fluids.

DETAILED DESCRIPTION OF THE PREFERRED EMBODIMENTS

The interface needle according to the present invention addresses a problem of mixing between two liquids delivered through a catheter. The interface needle is particularly useful for creating a blunt interface between a biocompatible solvent and a liquid embolic composition which are delivered to the body for treating aneurysms, arteriovenous malformations, arteriovenous fistula, incontinence, head and neck tumors, for sterilization, and peripheral applications. Examples of embolizing compositions are described in U.S. Pat. No. 5,695,480, which is incorporated herein by reference in its entirety. In addition, systems and methods for delivering embolizing compositions are described in U.S. Pat. No. 5,830,178, which is incorporated herein by reference in its entirely.

Although the present invention is particularly suitable for creating a blunt liquid interface between dimethylsulfoxide (DMSO) and a biocompatible polymer composition, it should be understood that the systems and methods of the present invention may be used for creating a blunt liquid interface between any two liquids delivered sequentially through a delivery system. The delivery system through which the liquids are delivered may be a catheter, cannula, needle, or the like. The term blunt interface means that mixing between the two liquids has been substantially reduced over conventional delivery methods.

The blunt liquid interface between the DMSO and a liquid embolic composition improves the delivery of the liquid embolic composition by allowing the formation of a small kernel or ball of polymer material during the initial injection, and preventing the formation of strands of polymer material which can be carried away in the bloodstream.

As shown in FIG. 1, the system for liquid delivery with a blunt liquid interface includes a catheter 10 or other cannula with a hub 28, an interface needle 12, and a syringe 14. The interface needle 12 includes a proximal end with a female luer fitting 18 for connection to a male luer fitting 20 of the syringe 14. A distal end of the interface needle 12 includes a male luer fitting 22 for connection to a female luer fitting 24 of the catheter hub 28.

As shown most clearly in the cross-sectional view of FIG. 2, the interface needle 12 includes a lumen 30 with a tapered portion 32. The tapered portion 32 tapers from a largest proximal dimension to a smallest distal dimension. The taper is provided at an angle A which is between about 10 and about 60 degrees, preferably between about 20 and about 40 degrees, and most preferably approximately 30 degrees. A hypo tube 36 is fitted within the lumen 30 and extends from the distal end of the male luer fitting 22. The hypo tube 36 may be overmolded, press fit, crimped in place, secured with adhesive, or otherwise secured inside the lumen 30 of the interface needle 12. The hypo tube 36 may also be replaced with another type of rigid or flexible tube.

The body of the interface needle 12 is preferably formed of a polymer material which is compatible with DMSO or other liquids being delivered, such as polypropylene, polyethylene, polyester, and the like. The hypo tube extends from the distal end of the male luer fitting 22 a distance sufficient to allow the typo tube to bypass a reservoir 38 in the catheter hub 28 and delivers the liquid directly into the catheter lumen. The length of the hypo tube 36 may vary depending on the type of catheter hub 28 used. For example, the hypo tube 36 may have a total length of about 0.2 to about 1.0 inches and a length extending from the distal end of the male luer 22 of about 0.05 to about 0.75 inches.

The hypo tube 36 is dimensioned to fit within the lumen of the catheter 10 forming a seal between the interface needle and the catheter lumen and bypassing any liquid in the reservoir 38 of the catheter hub 28. A diameter of the hypo tube 36 will vary depending on the internal diameter of the catheter 10 into which the hypo tube fits and forms a seal. Preferably, the interface needle 12 is provided in different sizes dimensioned to be used with different neuro catheters.

The procedure for delivering two liquids and achieving a blunt liquid interface according to the present invention is as follows. Initially, a first liquid is delivered directly to the catheter 10 with a first syringe. A second liquid is then provided in a second syringe and the interface needle 12 is connected to the second syringe. Air is expelled from the interface needle 12 by injection of fluid from the second syringe. The second liquid is preferably injected to fill the entire interface needle 12 and hypo tube 36. The male luer fitting 22 of the interface needle 12 is then connected to the catheter hub 28 such that a blunt liquid interface is formed between a first liquid in the catheter 10 and a second liquid in the hypo tube 36. The second liquid is then delivered from the syringe 14 and interface needle 12 through the catheter 10.

Two or more liquids can be delivered to the catheter in sequence with each of the liquids after the first liquid being delivered by a separate syringe having an interface needle attached.

When the present invention is used to deliver a liquid embolic composition with a blunt or even interface between a biocompatible solvent and a liquid embolic composition, the procedure employed is as follows. The syringe 14 is filled with the liquid embolic composition and the interface needle 12 is attached to the syringe. Air is expelled from the interface needle 12 by injection of liquid embolic composition through the interface needle with the syringe 14. The exterior of the interface needle 12 is preferably cleaned. The interface needle 12 is then attached to the catheter hub 28 of a catheter which has been previously flushed with DMSO or other biocompatible solvent. The liquid embolic composition is injected slowly to create a blunt liquid interface between the DMSO and liquid embolic composition and prevent dilution of the two fluids at the liquid interface. The blunt liquid interface created by the interface needle 12 has been found to travel down the length of the catheter to a delivery site with minimal mixing between the two liquids.

The interface needle according to the present invention is easy to use, achieves repeatable results, and substantially reduces the amount of mixing occurring between two liquids which are delivered in sequence.

The blunt liquid interface provides a reduction in dilution which occurs at the leading edge of the second fluid being delivered. This reduces the amount of change in viscosity of the second liquid. When using a liquid embolic composition the more uniform viscosity improves the deliverability of the liquid embolic composition. In contrast, when the liquid embolic composition is delivered directly to the catheter hub 28, the large open space within the catheter hub allows substantial mixing. When the liquid embolic composition injection is begun within a confined space such as the lumen of the catheter 10, mixing of the liquid embolic composition and solvent is greatly reduced. The more abrupt liquid interface also improves the ability to visualize the leading edge of the polymer composition being delivered.

FIG. 4 illustrates an alternative embodiment of an interface needle 50 which is configured to allow delivery of a high viscosity fluid without rupturing the delivery system. One option for providing delivery of high viscosity fluids, such has fluids having viscosities of at least 150 cSt at 40° C., to the vasculature is to provide high-pressure delivery systems. However, catheters which are designed with reinforcing to withstand high pressure fluid delivery lack one or more of the desirable catheter features including trackability, pushability, flexibility, and ability to be manipulated without trauma to the vasculature.

The interface needle 50 provides a solution to the high-pressure delivery problem by providing a pressure relief mechanism between a syringe and a catheter allowing non-reinforced catheters to be used. The interface needle 50 is designed to manage the high pressures of injection of high viscosity fluid before the fluid enters a catheter or other delivery system. The interface needle 50 preferably will also create an abrupt liquid interface in the manner as the interface needle 12 of FIGS. 1–3.

As shown in FIG. 4, the interface needle 50 includes a high pressure tube 52. a female luer fitting 54 at a first end of the tube, and a male luer fitting 56 at a second end of the tube. An overmolding 60 preferably covers the tube 52 and provides an ergonomic exterior of the interface needle 50. As in the interface needle of FIGS. 1–3, a hypo-tube 58 extends from the male luer fitting 56 for bypassing a reservoir in a catheter hub. The tube 52 and any coatings and overmoldings are formed of a material and a configuration to provide sufficient strength, internal configuration, and length to accommodate and contain high-pressure injection.

In operation, the first end 54 of the interface needle 50 is connected to a syringe containing a high viscosity fluid and the second end 56 is connected to an unreinforced catheter. High viscosity fluid is then injected at high pressures through the interface needle 50 which dynamically reduces the pressure sufficiently within the needle so that the fluid can be delivered to an unreinforced catheter, preferably an unreinforced neuro catheter without rupture of the catheter. Preferably, the pressure of injection is reduced to approximately 350 psi or less at the second end 56 of the interface needle 50. The length of the interface needle 50 will vary depending on the initial injection pressure at the first end 54 of the interface needle and the change in pressure which is needed to achieve a desired exit pressure. For example, the tube 52 may have a length of about 0.5 inches about 15 inches, preferably about 1 inch or greater.

The tube 52 may be metal or plastic and may be overmolded, coated, or reinforced for purposes of ergonomic design or improved functionality. An inner diameter of the tube 52 is preferably substantially the same as the inner diameter of the catheter to be connected to the interface needle. The tube 52 may have tapered inner diameter with the distal end inner diameter being substantially the same as a proximal inner diameter of the catheter.

The interface needle 50 according to the present invention is particularly useful for controlled delivery of high viscosity liquid embolic compositions with at least twelve percent polymer and/or with viscosities of at least 150 cSt at 40° C. as described in U.S. patent application Ser. No. 09/574,379, entitled "Novel High Viscosity Embolizing Compositions" filed on even date herewith, which is incorporated herein by reference in its entirety.

For delivery of liquid embolic compositions having viscosities of between about 500 and about 5000 cSt at 40° C., the pressure of the composition delivered from a 1 cc syringe can be about 3000 to about 4000 psi. The pressure reduction which is needed for delivery of this composition through a catheter delivery system depends on the catheter to be used. Known flow directed neuro catheters are burst rated at 100 psi and have actual burst strengths of 150 psi. Guidewire directed neuro catheters have burst strengths of about 200 to about 400 psi. Reinforced neuro catheters having higher burst strengths of 1000 psi or greater are also available, however, these reinforced catheters lack the greater flexibility of the unreinforced catheters which is often desirable.

According to one example of the invention, the interface needle 50 is configured to provide a pressure drop from about 3000–4000 psi at the first end 54 to about 300–350 psi at the second end 56 for delivery of a liquid embolic composition having a viscosity of about 1100 cSt at 40° C. through a guidewire directed, unreinforced neuro catheter.

Although the interface needle 50 of the present invention has been described with respect to high viscosity liquid embolic compositions, it should be understood that the interface needle 50 may also be used for delivering other fluid compositions where it is important to prevent excessive fluid pressure from being applied to a delivery system.

While the invention has been described in detail with reference to the preferred embodiments thereof, it will be apparent to one skilled in the art that various changes and modifications can be made and equivalents employed, without departing from the present invention.

What is claimed is:

1. A device for creating a blunt interface between liquids delivered using a cannula having a lumen and a hub with a reservoir disposed therein, the device comprising:

a body having a proximal end configured for connection to a syringe and a distal end opposite the proximal end configured to be attached to the cannula hub;

a tapered lumen extending through the body from the proximal end to the distal end, the tapered lumen having a first diameter at the proximal end and a second smaller diameter at the distal end; and a tube which extends from the distal end of the body to the lumen of the cannula when the distal end of the body is attached to the cannula hub such that liquid is delivered directly to the lumen of the cannula bypassing the reservoir in the cannula hub.

2. The device of claim 1, wherein, the tube has a length of about 0.05 to about 0.75 inches from a distal end of the body to a distal end of the tube.

3. The device claim 1, wherein the body has a length of greater than 0.5 inches.

4. The device of claim 1, wherein the body and tube are formed of a DMSO compatible material.

5. A system for creating a blunt interface between liquids delivered using a cannula having a lumen and a hub with a reservoir disposed therein, the system comprising:

a syringe;

a cannula having a cannula lumen and a cannula hub with a female luer fitting and a reservoir within the cannula hub; and a bypass device connectable to the syringe and the cannula hub, the bypass device having a tube which extends from the bypass device to the lumen of the cannula when the bypass device is connected to the cannula hub such that liquid is delivered directly to the lumen of the cannula bypassing the reservoir in the cannula hub.

6. The system of claim 5, wherein the bypass device includes a tapered lumen tapering from a largest dimension at an end connectable to the syringe and a smallest dimension at an end connectable to the cannula hub.

7. The system of claim 5, wherein the tube is dimensioned to fit into the cannula lumen.

8. The system of claim 1, wherein the tube has a length of about 0.05 to about 0.75 inches from a distal end of a body of the bypass device to a distal end of the tube.

9. The system of claim 5, wherein the cannula is a catheter.

10. The system of claim 5, wherein the cannula is a needle.

11. A method of delivering two liquids comprising:

delivering a first liquid through a cannula with a first syringe;

removing the first syringe from the cannula;

attaching a second syringe to a bypass device for creating a blunt liquid interface, the bypass device bypassing a reservoir in the cannula hub such that the second liquid is delivered directly to a lumen of the cannula;

connecting the bypass device to the cannula; and delivering a second liquid with the second syringe to create a blunt liquid interface between the first and second liquids.

12. The method of claim 11, wherein the bypass device includes a first end connectable to the syringe, a second end connectable to a hub of the cannula, and a tube for delivering liquid directly to a lumen of the catheter bypassing a reservoir in the cannula hub.

13. The method of claim 11, wherein the second fluid is injected into the bypass device to remove air from the bypass device before connecting the bypass device to the cannula.

14. A method of delivering high viscosity liquids with viscosities of at least 150 cSt at 40° C., the method comprising:

providing a syringe containing the high viscosity liquid;

connecting the syringe to a first end of a pressure relief interface needle;

connecting a second end of the pressure relief interface needle to a delivery cannula;

injecting the high viscosity liquid with the syringe; and reducing an injection pressure to about 350 psi or less at the second end of the interface needle.

15. The method of claim 14, wherein the interface needle has a tapered inner lumen.

16. A system for delivering high viscosity liquids with viscosities of at least 150 cSt at 40° C., the system comprising:

a syringe;

a pressure reducing device configured to be connected to a first end of the syringe and to reduce a pressure of the high viscosity fluid being delivered from about 3000–4000 psi down to 350 psi or less; and a neuro catheter configured to be connected to a second end of the syringe.

17. The system of claim 16, wherein the pressure reducing device has a length of at least 1 inch.

18. The system of claim 16, wherein the pressure reducing device has a tapering lumen.

19. The system of claim 16, wherein the neuro catheter is a flow directed catheter, and the pressure of the high viscosity fluid is reduced down to 150 psi or less.

* * * * *